(12) United States Patent
Schneider et al.

(10) Patent No.: US 8,119,709 B2
(45) Date of Patent: Feb. 21, 2012

(54) ACOUSTIC WAVEGUIDE ARRAY

(75) Inventors: John K. Schneider, Snyder, NY (US); Jack C. Kitchens, Tonawanda, NY (US)

(73) Assignee: Ultra-Scan Corporation, Amherst, NY (US)

( * ) Notice: Subject to any disclaimer, the term of this patent is extended or adjusted under 35 U.S.C. 154(b) by 23 days.

(21) Appl. No.: 12/555,220

(22) Filed: Sep. 8, 2009

(65) Prior Publication Data

US 2010/0052827 A1    Mar. 4, 2010

Related U.S. Application Data

(63) Continuation-in-part of application No. 11/761,101, filed on Jun. 11, 2007, now Pat. No. 7,745,521.

(60) Provisional application No. 60/804,412, filed on Jun. 9, 2006.

(51) Int. Cl.
   *C08K 5/15*    (2006.01)
   *H01P 3/00*    (2006.01)

(52) U.S. Cl. .................................. 524/114; 333/242

(58) Field of Classification Search .................... 524/114
See application file for complete search history.

(56) References Cited

U.S. PATENT DOCUMENTS

| | | | |
|---|---|---|---|
| 4,012,650 A | 3/1977 | Pratt et al. | |
| 4,077,023 A | 2/1978 | Boyd et al. | |
| 4,742,318 A | 5/1988 | Jen et al. | |
| 4,743,870 A | 5/1988 | Jen et al. | |
| 5,005,005 A | 4/1991 | Brossia et al. | |
| 5,596,671 A * | 1/1997 | Rockwell, III | 385/147 |
| 5,828,274 A * | 10/1998 | Jen et al. | 333/143 |
| 2003/0044149 A1 | 3/2003 | Fraval et al. | |
| 2003/0053936 A1 * | 3/2003 | Potyrailo et al. | 422/82.11 |
| 2003/0073904 A1 | 4/2003 | Moriya et al. | |
| 2006/0072875 A1 | 4/2006 | Bhagavatula et al. | |
| 2008/0219098 A1 | 9/2008 | Schneider et al. | |

FOREIGN PATENT DOCUMENTS

| WO | WO 2008/036444 A2 | 3/2008 |
|---|---|---|
| WO | WO 2008/066956 A2 | 6/2008 |

OTHER PUBLICATIONS

Jen; Acoustic Fibers; 1987 IEEE; 1987 Ultrasonics Symposium; pp. 443-454.
Jen, et al.; Clad polymer buffer rods for polymer process monitoring; Ultrasonics 39 (2001); pp. 81-89.
Legros, et al.; Ultrasonic evaluation and application of oriented polymer rods; Ultrasonics 37 (1999); pp. 291-297.
Verdonk; Measurements of Pulse Mode Behavior in Weakly-Clad Silica Waveguides; 1996 IEEE Ultrasonics Symposium; pp. 723-726.
Industrial Materials Institute / National Research Council; Flexible Piezoelectric/Ultrasonic Sensors for Biomedical Applications; Industrial Materials Institute / National Research Council; 1 page.
Industrial Materials Institute / National Research Council; Integrated (IUT) and Flexible Ultrasonic Transducers (FUTs) Technology for Real-Time On-site Nondestructive Evaluation; Industrial Materials Institute / National Research Council; 1 page.
Jen; Similarities and Differences Between Fiber Acoustics and Fiber Optics; 1985 Ultrasonics Symposium; 1985 IEEE; pp. 1128-1133.
Jen et al.; Leaky Modes in Weakly Guiding Fiber Acoustic Waveguides; IEEE Transactions on Ultrasonics, Ferroelectrics, and Frequency Control, vol. UFFC-33, No. 6, Nov. 1986; pp. 634-643.

* cited by examiner

*Primary Examiner* — Ling Choi
*Assistant Examiner* — Hui Chin
(74) *Attorney, Agent, or Firm* — Hodgson Russ LLP (57) ABSTRACT

An acoustic (sound or ultrasound) wave transmitter having a plurality of waveguides is described, and a method of making such a transmitter is described. Each waveguide can have a cladded core. The cladded core is capable of transmitting acoustic wave energy from a first end surface to a second end surface of the cladded core. The waveguides can be substantially fixed relative to each other by a binder. The binder can be formed by fusing the claddings together, potting a material between the waveguides and/or mechanically holding the waveguides.

24 Claims, 6 Drawing Sheets

FIG. 3A SEPARATE FIBERS WITH CORE & CLADDING

FIG. 3B FIBERS WITH CORE & CLADDING UNDERGOING FUSING

FIG. 3C FULLY FUSED FIBERS WITH CORE INTACT & CLADDING NOW CONTINUOUS

ACOUSTIC WAVEGUIDE ARRAY

CROSS-REFERENCE TO RELATED APPLICATIONS

This application is a continuation-in-part of U.S. patent application Ser. No. 11/761,101, which was filed on Jun. 11, 2007. Ser. No. 11/761,101 claims the benefit of priority to U.S. provisional patent application Ser. No. 60/804,412, filed on Jun. 9, 2006. This continuation-in-part patent application also claims the benefit of U.S. provisional patent application Ser. No. 60/804,412.

FIELD OF THE INVENTION

The present disclosure relates to devices for transmitting information using longitudinal waves, such as sound and ultrasound. The term "acoustic" is used to refer collectively to sound waves and ultrasound waves.

BACKGROUND

It is known to use acoustic waves, such as ultrasonic energy, to determine information about an object. For example, in non-destructive testing, ultrasonic energy pulses are used to determine whether flaws exist in an object without damaging the object. Ultrasonic energy pulses are also used to obtain information about the friction ridge surfaces, such as fingerprints, of human beings.

To use an ultrasonic energy pulse to obtain information, the pulse must be sent from a device (the "emitter") that is suitable for emitting ultrasonic energy pulses toward an object to be analyzed, and there must be a device (the "receiver") that is suitable for receiving the energy once it has been reflected by or passed through the object. For ease of description, we will discuss the situation in which ultrasonic energy is reflected, but it will be recognized that this description can be applicable to situations in which the detected ultrasonic energy passes through the object being analyzed. Furthermore, in order to illustrate the concepts and ideas, the object being analyzed is from time to time described as a fingerprint, but it will be recognized that this invention is not limited to fingerprint scanners.

When the object being analyzed is a fingerprint, a single device can be used to serve as both the emitter and the receiver. Usually, the emitter and the receiver are positioned some distance from the object being analyzed, and so the emitted ultrasonic energy and the reflected ultrasonic energy must travel through a transmittive substance. Air is a transmittive substance for ultrasonic energy, but other substances transmit ultrasonic energy better than air. One such transmittive substance is mineral oil.

BRIEF SUMMARY OF THE INVENTION

The invention can be implemented as an acoustic wave transmitter having a plurality of waveguides. Although this document focuses on ultrasound, this is done to illustrate one implementation. Other implementations can not be limited to ultrasound, and it should be recognized that other acoustic waves can be used.

Each waveguide can have a core and cladding. The core can have a first end surface, a second end surface, and a longitudinal surface extending between the first and second end surfaces. The longitudinal surface of the core can be substantially surrounded by the cladding to form a cladded core. The cladded core is capable of transmitting ultrasonic energy from the first end surface to the second end surface.

The waveguides can be substantially fixed relative to each other by a binder. The binder can be formed by fusing the claddings together, potting a material between the waveguides and/or mechanically holding the waveguides.

The core can be a material having a first shear-wave propagation velocity ("SWPV"). The cladding can be a material having a second shear-wave propagation velocity, and the first SWPV is different from the second SWPV. The second SWPV can be greater than the first SWPV.

The invention can be implemented as a method of making an acoustic wave transmitter. In one such method, a plurality of waveguides are provided. Each wave guide has a core and cladding. The core has (a) a first end surface, (b) a second end surface, and (c) a longitudinal surface extending between the first and second end surfaces. The cladding substantially surrounds the core to form a cladded core. The core can have a first shear-wave propagation velocity ("SWPV"), and the cladding can have a second SWPV. The second SWPV is greater than the first SWPV.

Each of the plurality of waveguides can be substantially fixed to at least one other waveguide, thereby binding the waveguides. The binding operation can be carried out by heating the waveguide to fuse the cladding of at least one waveguide to the cladding of another waveguide. Also, the binding operation can be carried out by potting the waveguides with a suitable potting material placed between the waveguides. Finally, the binding operation can be carried out by placing a band around the plurality of waveguides.

The waveguides can be cut to a desired length. For example, the waveguides can be cut prior to or after the binding operation. In one implementation, the cutting operation is carried out so that the first end surfaces of the waveguides lie substantially in a plane. Further, the cutting operation can be carried out so that the second end surfaces of the waveguides lie substantially in a different plane.

BRIEF DESCRIPTION OF THE SEVERAL VIEWS OF THE DRAWINGS

For a fuller understanding of the nature and objects of the invention, reference should be made to the accompanying drawings and the subsequent description. Briefly, the drawings are.

DETAILED DESCRIPTION OF THE INVENTION

FIGS. 1A through 1E depict one implementation in which a plurality of substantially parallel ultrasonic waveguides 1 are held together into a single assembly. The assembly is shown in FIG. 1 as an array 6 of waveguides 1. The ultrasonic waveguides 1 can be fibers, and can be thought of as conduits that transmit acoustic wave energy, such as ultrasonic energy, from a first end-surface 8 of the waveguide 1 to a second end-surface 10 of the waveguide 1. Each waveguide 1 in the waveguide array 6 can be used to convey a different ultrasonic signal from one side of the waveguide array 6 to the other side. In order to preserve the information being transmitted by the waveguides, the relative positions of the first end-surfaces 8 of the waveguides 1 can be positioned substantially the same as the relative positions of the second end-surfaces 10 of the waveguides 1.

Figures 1A, 1B, 1C, 1D, 1E:
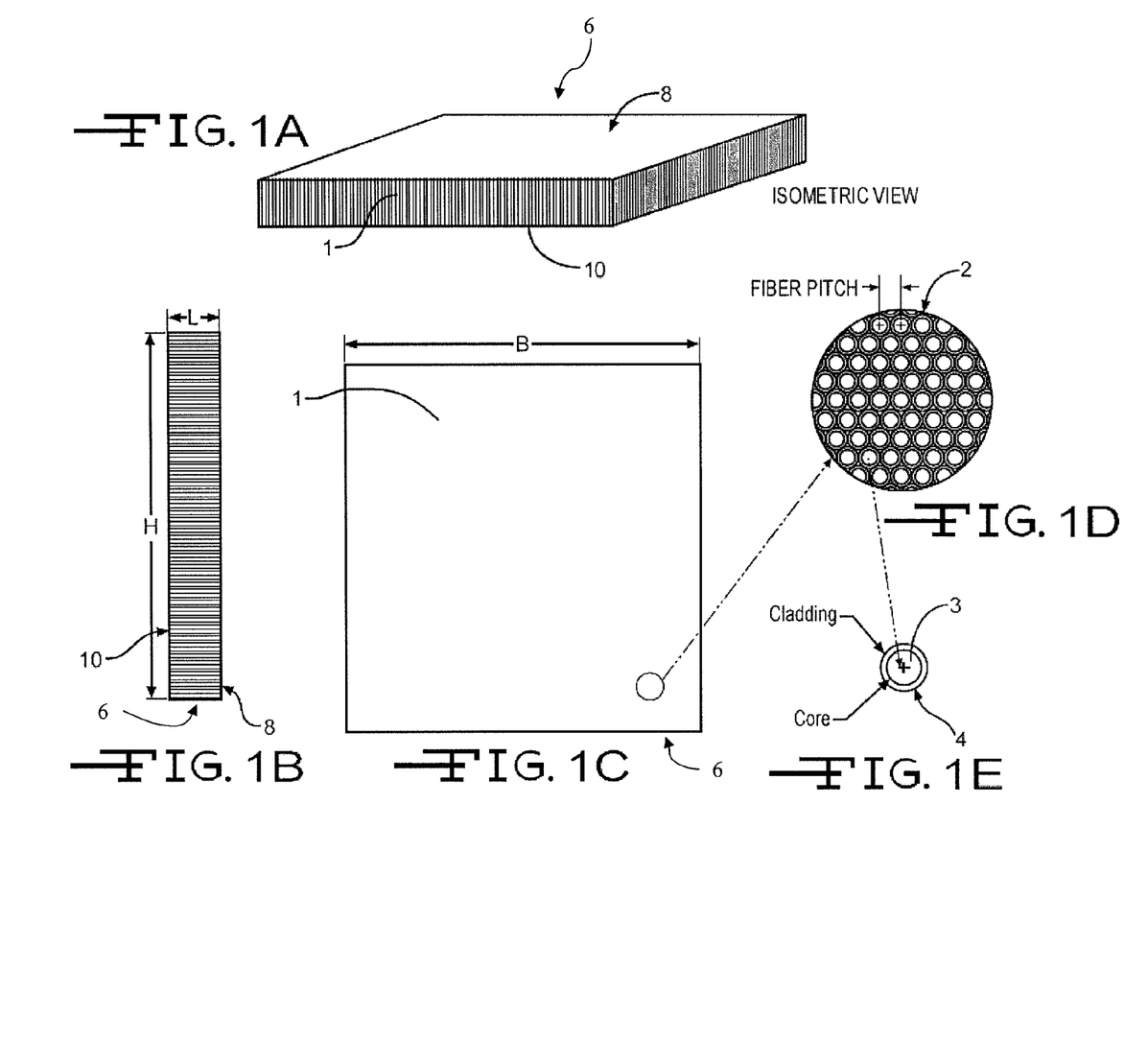
FIG. 1A is an isometric view of an ultrasonic wave transmitter according to one implementation.
FIG. 1B is a side view of the transmitter depicted in FIG. 1A.
FIG. 1C is a plan view of the transmitter depicted in FIG. 1A.
FIG. 1D is an enlarged view of a portion of the transmitter depicted in FIG. 1C.
FIG. 1E is an enlarged view of a waveguide depicted in FIG. 1D.

In one implementation, an assembly of waveguides 1 is formed so that ultrasonic energy can be conducted from one side of the assembly to the other side. The waveguides 1 can be constructed to have a core 3 material and a cladding 4 material. The core 3 and cladding 4 can be substantially solid. The propagation velocity of a shear-wave in the core 3 material should differ from the propagation velocity of a shear-wave in the cladding 4 material so that an ultrasonic wave traveling through the waveguide 1 is substantially contained in the waveguide 1 by means of total internal reflection at the interface of the core 3 and cladding 4. Since ultrasonic energy can be used to transmit information, such as fingerprint information, this implementation can be used to transmit information about a pattern (such as a fingerprint) from one side of the waveguide array 6 to another side of the waveguide array 6.

Such an array 6 can be used, for instance, in ultrasonic fingerprint imaging. In this situation, ultrasonic pulses are reflected from a finger. Generally, the finger 50 is placed on a platen, and when the ultrasonic energy arrives at the finger, at the valleys of the fingerprint all or nearly all of the energy is reflected back. At the ridges of the fingerprint, most of the energy is absorbed by the finger 50 and only a small quantity of ultrasonic energy is reflected back. At the ridge-valley transition region of the fingerprint, the energy reflected back will be between these two values. The detector then measures the amount of energy received, and then a computer translates that value into a grey scale image that is displayed on a monitor. The waveguide array 6 can be placed in the path of the emitted ultrasonic pulse and/or the reflected ultrasonic energy so as to transmit the ultrasonic energy in a manner that minimizes losses and scattering of ultrasonic energy.

Figure 6:
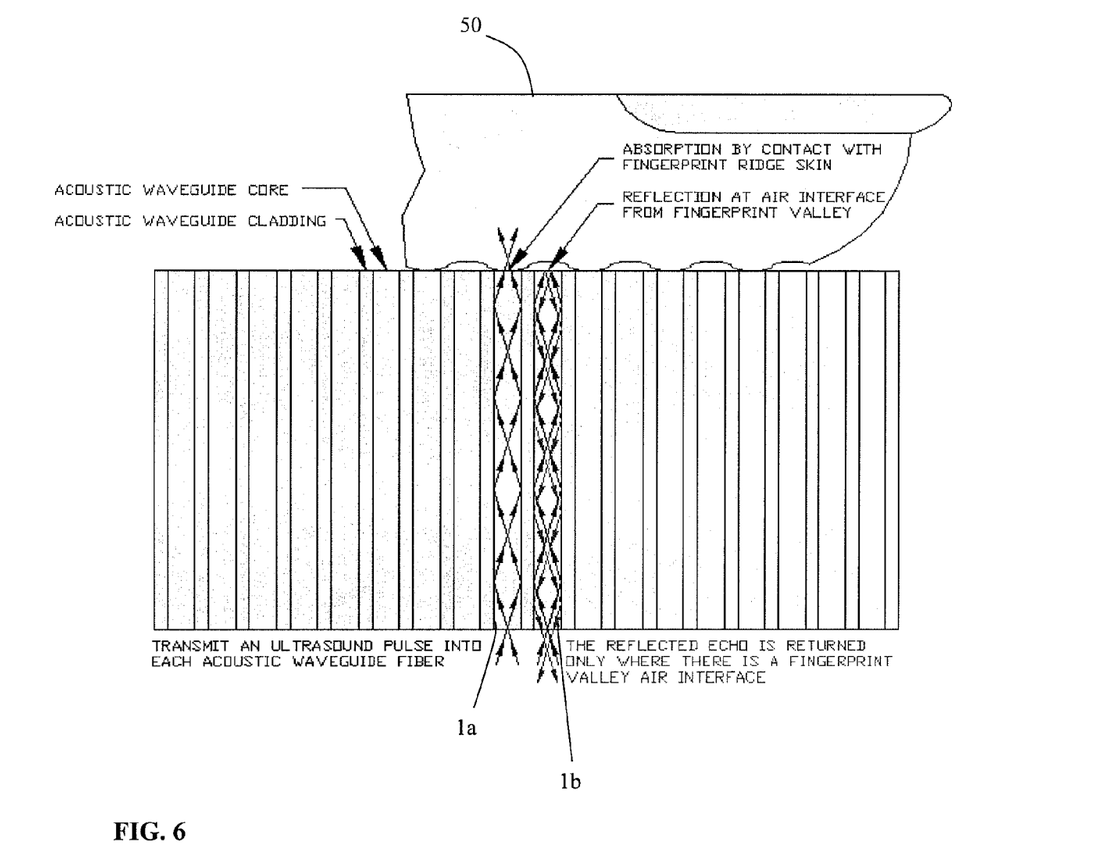
FIG. 6 illustrates how the invention can operate.

In FIG. 6, there is shown a waveguide array 6. Two of the waveguides illustrate ultrasonic energy being transmitted. In the waveguide 1a, ultrasonic energy is shown traveling to the finger. In the waveguide 1b, ultrasonic energy is shown traveling to and from the finger. Note that the energy transmitted to the finger 50 is absorbed in the case of waveguide 1a because the skin of the finger 50 contacts the platen, but in the case of waveguide 1b the ultrasonic energy is reflected at the platen because air (not skin) contacts the platen.

This system could be used for vascular imaging by applying the platen surface to the skin near the blood vessel to be imaged, and using an appropriate coupling gel. By proper selection of a range gate distance within the tissue, the imaging surface can be extended past the platen surface and the blood vessels imaged by careful examination of the returning echo. Since the various tissue interfaces are all of differing acoustic impedance, they will reflect differently and an image can be created by examination of the returned ultrasonic signals arriving at the detector at the time corresponding to the depth of the blood vessels to be imaged.

Figures 2A, 2B:
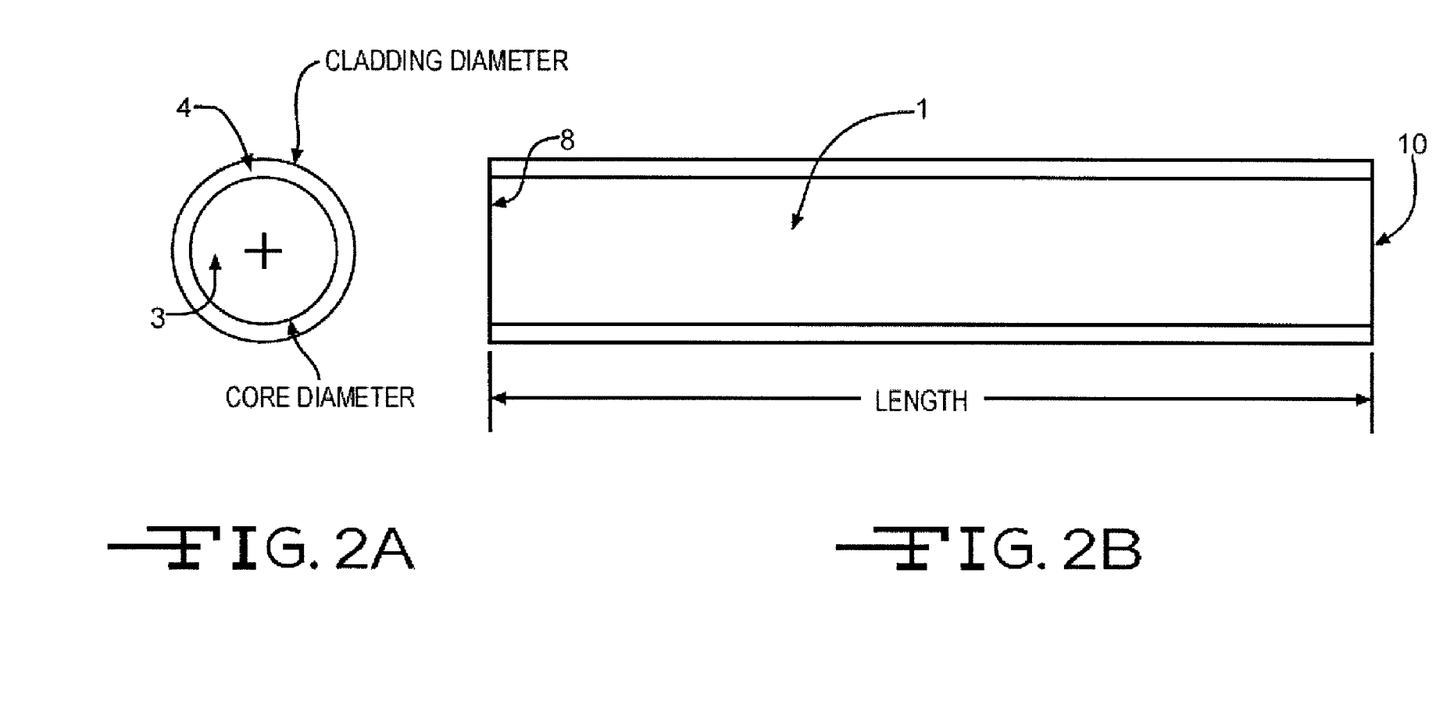
FIG. 2A is an end view of a waveguide.
FIG. 2B is a side view of a waveguide.

Having described some implementations in general terms, further details are now provided. Each waveguide 1 has a core 3 and cladding 4. FIGS. 2A and 2B depict a waveguide 1. The materials of the core 3 and cladding 4 are selected so that the shear-wave velocity of the cladding 4 is greater than the shear-wave velocity of the core 3. By carefully selecting the core 3 and cladding 4 materials, sound traveling within the waveguide 1 is substantially confined to the core 3.

Under these conditions, acoustic waves, such as ultrasonic waves, are allowed to propagate along the length of the waveguide 1. The core/cladding interface reflects the shear wave. This condition prevents leakage of the wave energy through the cladding 4. The greater the differences in shear-wave velocities between the core 3 and cladding 4, the thinner the cladding 4 can be. When ultrasonic energy waves are confined primarily to the core 3 material, external conditions will have little or no significant effect on transmission of the ultrasonic energy.

Although it would be an easy matter to simply select two materials for the core 3 and cladding 4, manufacturing, chemistry and physics considerations limit the choices. For example, the materials selected for the core 3 and cladding 4 of a waveguide 1 should have a similar softening temperature and uniformity of extrusion. In this manner, the waveguide 1 can be more easily and cheaply manufactured.

Furthermore, in order to propagate through the waveguide 1, the ultrasonic energy should have a wavelength corresponding to a frequency that is at or above a cutoff frequency of the waveguide 1. The cutoff frequency for the waveguide 1 can be determined by:

$$f_c = V_s / 2d$$

where "$f_c$" is the cutoff frequency, "$V_s$" is the shear velocity (the velocity perpendicular to the longitudinal velocity vector) of the core 3 and "d" is the diameter of the core 3. Based on the relative differences in shear-wave propagation of the core 3 and cladding 4 materials, the ratio of core 3 diameter to the minimum cladding 4 thickness can be determined. For example, the thickness of the cladding 4 can be determined using Bessel functions, or determined empirically by experimentation.

Successful waveguides have been created using waveguides 1 having a core diameter of 41 micrometers of polystyrene dispersed in a cladding matrix of polymethylmethacrylate, and arranging the cores 3 in a hex pattern geometry in which the center-to-center distances of the waveguides is about 50 micrometers. This size is particularly suitable for 500 dot-per-inch fingerprint scanning systems. Successful systems have also been produced with cores 3 having diameters of 250 micrometers, 100 micrometers, 25 micrometers and 3 micrometers in suitably spaced cladding matrices.

Figure 5:
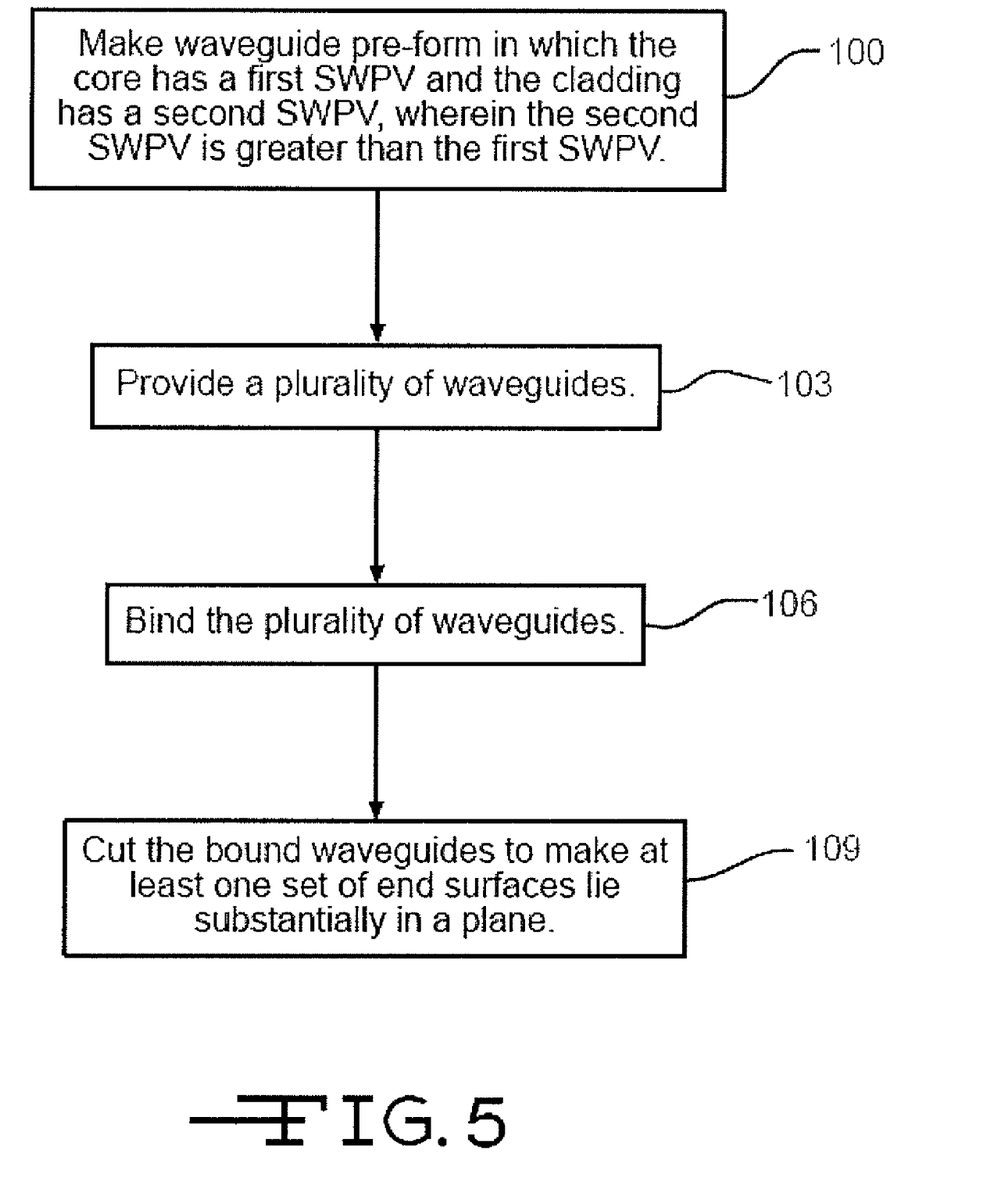
FIG. 5 depicts a method according to one implementation.

FIG. 5 depicts a method in which the plurality of waveguides 1 are made into an acoustic wave transmitter. To manufacture a waveguide 1, a waveguide pre-form is made 100. To do so, a cylinder of the core 3 material can be prepared of a nominal diameter. Similarly, a hollow cylinder of the cladding 4 material can be prepared with an inner diameter similar to that of the core 3 and an outer diameter proportional to the core cladding ratio desired by the waveguide designer.

A core 3 and cladding 4 can be nested together and heated in an oven until they fuse, thereby forming a waveguide pre-form. Successful waveguide fibers can be made by starting with a 5 inch diameter of Polymethylmethacrylate ("PMMA") hollowed out with an inner diameter of approximately 4 inches, to which a 4 inch diameter solid cylinder of polystyrene can be nested. After fusing, this assembly can be drawn (pulled to make a smaller diameter) to the appropriate dimensions to achieve a material of the proper size cores 3 in a process where successively smaller draws are combined, fused and redrawn to reach the final dimensions for a properly sized waveguide 1. When at the proper size, the drawn waveguide 1 can be cut perpendicular to the longitudinal axis of the waveguide 1 axis. A plurality of the cut waveguides 1 can be assembled into an array 6, and the ends of the waveguides 1 are polished to form a plate having two flat surfaces.

In another method of making a waveguide array 6, a glass capillary is filled with polystyrene resin. For example, styrene monomer can be wicked in a glass capillary, and the monomer can be polymerized in-situ. In another process, molten polystyrene resin is injected into the glass capillary using an injection molding ram.

Also, a polystyrene capillary can be filled with polymethylmethacrylate resin to form a waveguide pre-form. It will be recognized that a waveguide pre-form can be made by filling a plastic capillary with an appropriate material having the required shear-wave propagation velocity characteristic.

Once the waveguide pre-form is made, the pre-form can be drawn to the desired diameter using standard fiber extrusion and drawing techniques. Such techniques are commonly used to manufacture poly-thread and fiber, such as monofilament fishing line. In manufacturing a waveguide 1, suitable polymers can be selected for the core 3 and cladding 4.

Figure 3A:
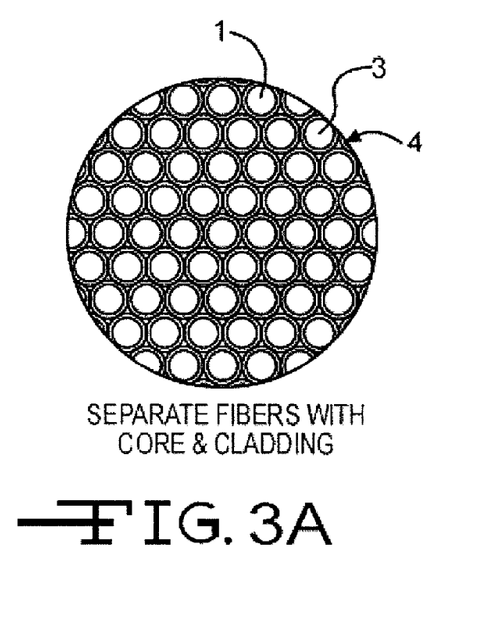
FIG. 3A depicts an assembly of waveguides that have not been fixed relative to each other.
Figure 3B:
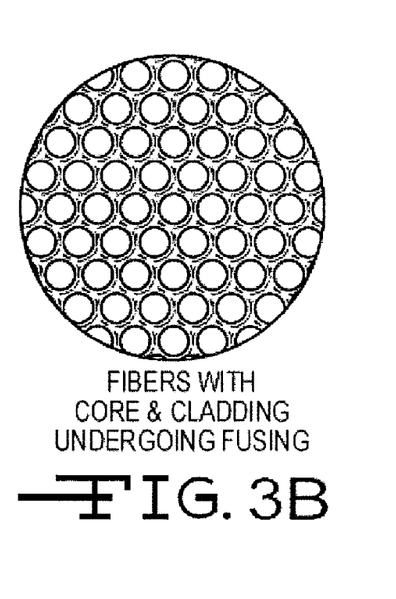
FIG. 3B depicts an assembly of waveguides for which the claddings are beginning to fuse.
Figure 3C:
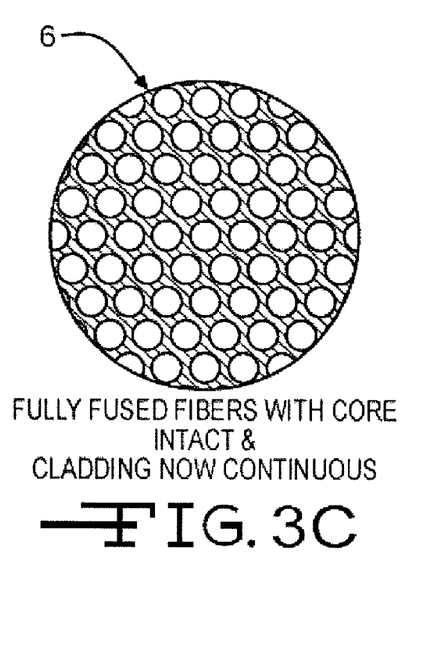
FIG. 3C depicts an assembly of waveguides for which the claddings have fused so as to fix the position of the waveguides relative to each other.

Once the core 3 and cladding 4 have been drawn to the desired diameter, the resulting fiber can be cut into appropriate lengths, to form a plurality of waveguides 1. The cutting operation can be carried out so as to provide a plurality of waveguides 1 having similar lengths. The plurality of waveguides can be provided 103 and carefully placed close to each other in order to provide a bundle of waveguides 1. FIG. 3A depicts a bundle of waveguides 1. To form the waveguide array 6, each waveguide is bound 106 in order to substantially fix each waveguide 1 to at least one of the other waveguides 1 in the bundle. To accomplish this, the bundle can be heated to fuse the claddings 4 to each other, and exclude interstitial air or gases. FIG. 3B depicts the waveguides 1 while the claddings 4 are fusing, and FIG. 3C depicts the waveguides 1 once fusing is complete.

Figure 4A:
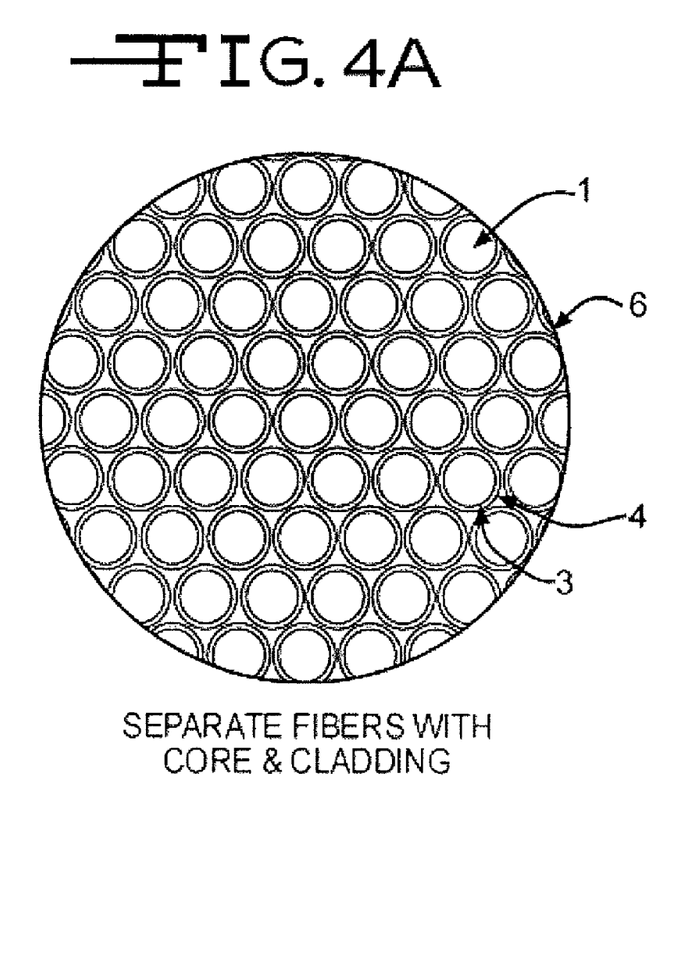
FIG. 4A depicts an assembly of waveguides that have not been fixed relative to each other.
Figure 4B:
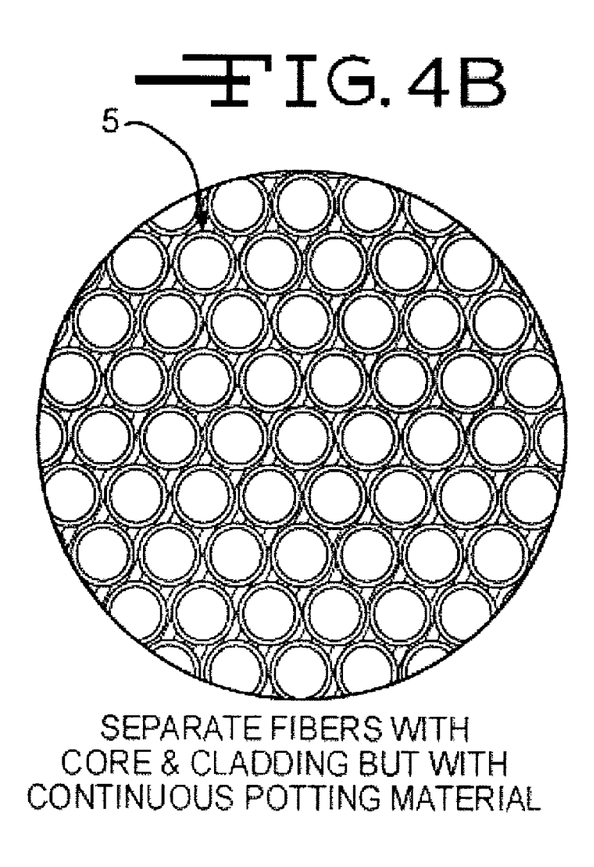
FIG. 4B depicts an assembly of waveguides that have been potted so as to fix the position of the waveguides relative to each other.

Alternatively, the interstices between the waveguides 1 can be filled in order to pot the waveguides 1 by using a suitable potting compound 5, such as a two part curing resin system. Epoxy resin systems or a room-temperature vulcanizable silicone rubber are two widely known means that can be used as a potting compound 5. FIG. 4A depicts the waveguides 1 prior to potting, and FIG. 4B depicts the waveguides 1 after potting.

In lieu of (or in addition to) potting or fusing the waveguides 1, the waveguides 1 can be mechanically constrained so that the end surfaces 8, 10 of the waveguides 1 are not permitted to move relative to each other. For example, a tightly drawn band can be used to mechanically constrain the waveguides 1.

Once bundled together, the resulting device can be thought of as an assembly having substantially parallel waveguides 1, each having a position that is fixed relative to the other waveguides 1 in the assembly. The assembly of waveguides 1 can be cut 109 perpendicular to the longitudinal axes of the waveguides 1 to provide an array 6 having a desired thickness. In this fashion, the first end-surfaces 8 can lie substantially in a plane. Further, the second end-surfaces 10 can lie substantially in a plane. The end surfaces 8, 10 of the waveguides 1 can be polished to a suitable flatness to prevent diffraction losses as the ultrasonic energy enters and leaves the waveguides 1.

One set of materials that can offer the qualities needed to create an ultrasonic waveguide 1 and ultimately the waveguide array 6 can be PMMA for the core 3 and polystyrene ("PS") for the cladding 4. Another polymer pair that can be used is polyethylene for the core 3 and polycarbonate for the cladding 4, although this pair can be more difficult to process because the melting points of these materials are not similar. Further, polystyrene can be used for the core 3 and glass can be used for the cladding 4. These are only examples of the types of materials that can be used. Other polymer or copolymer pairs can be successfully used to create a suitable ultrasonic waveguide 1, and subsequently the waveguide array 6.

The waveguide array 6 offers an inexpensive means of transmitting acoustic wave energy from one place to another, and does so with a minimum of signal loss. The waveguide array 6 can be used to transmit ultrasonic energy from an ultrasonic wave emitter to a finger, and/or from a finger to an ultrasonic wave receiver, as part of a system for producing a fingerprint image corresponding to the finger. In one such system, an ultrasonic wave guide waveguide array 6 is provided and a finger 50 is placed proximate to a first end surface 8 of the waveguides 1. Ultrasonic energy can be provided by an emitter, and the energy can travel to the finger 50 at least in part via the waveguide array 6. Some of the energy provided to the finger 50 can be reflected back toward the waveguide array 6. The reflected ultrasonic energy from the finger 50 can be received at first end-surfaces 8 of the waveguides 1 and transmitted via the waveguides 1 to the second end-surfaces 10 of the waveguides 1. The ultrasonic energy leaving the second end-surfaces 10 of the waveguides 1 can be provided to a receiver. The receiver can detect the ultrasonic energy received at various locations on the receiver, and convert the ultrasonic energy to one or more electric signals that are indicative of the strength of the received ultrasonic energy signal. The electric signals can be provided to a computer, which has software suitable for interpreting the electric signal and to generate an image of the fingerprint on a monitor.

In one type of waveguide system, the core 3 and cladding 4 are in intimate contact at their interfacial surfaces. The core 3 and cladding 4 can be selected to have different coefficients of thermal expansion. This difference can be exploited to achieve and maintain a compressive preload upon the core 3. During manufacture, a typical manufacturing method would be to fill an array of capillary cavities with molten core material and when the unit cools the core 3 will solidify, such that a solid core 3 and solid cladding 4 will be realized. If the cladding 4 material has a higher coefficient of thermal expansion than the core 3 material, and subsequently shrinks more than the core material during the cooling process, the compressive preload is realized and waveguide criteria are realized. If the situation is reversed and the core 3 material has a higher coefficient of thermal expansion than that of the cladding 3 material, then upon cooling the core may shrink away from the cladding 4 and spoil the waveguide function. This can be prevented by compressively loading the liquefied core 3 material while it is being introduced to the cladding 4. If the core 3 material is compressively loaded while liquid and the compressive loading is maintained when it solidifies, it will remain in compression during the cooling process and when it reaches its final ambient temperature will retain the compressive preload and the core 3/cladding 4 interface that will remain in intimate contact and waveguide function will be retained. It is possible, with sufficient preload, to maintain the compression in the cores 3 even at cold temperatures.

In one type of waveguide system, the core 3 and cladding 4 are in intimate contact at their interfacial surfaces. The materials selected for the core 3 and cladding 4 can be selected to have different coefficients of thermal expansion, and this difference can be exploited in order to achieve a compressive preload on the core 3. During manufacture, as the temperature of the assembly changes to a state where the core 3 shrinks more than the cladding 4 or the cladding 4 expands more than the core 3, which establishes a compressive preload due to the interfacial contact between the core 3 and cladding 4 surfaces.

This can be achieved by filling a capillary array of cladding material with molten core material. Pressure can be maintained on the core 3 while it solidifies (with injection molding equipment). When the part is at a nominal room temperature, the core material has maintained a compressive preload that remains with the unit through its service life.

Although the present implementation has been described with respect to one or more particular implementations, it will be understood that other implementations can be made without departing from the spirit and scope of the present invention. Hence, the present implementation is deemed limited only by the appended claims and the reasonable interpretation thereof.

What is claimed is:

1. An ultrasonic wave transmitter, comprising:
   a plurality of ultrasonic waveguides, each ultrasonic waveguide having a core and cladding, the core comprising (a) a first end surface, (b) a second end surface, and (c) a longitudinal surface extending between the first and second end surfaces, the longitudinal surface being substantially surrounded by the cladding to form a cladded core, wherein the core comprises a material having a first shear-wave propagation velocity ("SWPV"), and the cladding comprises polymethylmethacrylate having a second shear-wave propagation velocity, and wherein the second SWPV is greater than the first SWPV;
   a binder holding the ultrasonic waveguides so as to substantially fix each ultrasonic waveguide relative to the other ultrasonic waveguides.

2. The ultrasonic wave transmitter of claim 1, wherein the ultrasonic waveguides are substantially the same length.

3. The ultrasonic wave transmitter of claim 1, wherein the first end surfaces of the ultrasonic waveguides lie substantially in a plane.

4. The ultrasonic wave transmitter of claim 1, wherein the second end surfaces of the ultrasonic waveguides lie substantially in a plane.

5. The ultrasonic wave transmitter of claim 1, wherein the binder is a material substantially the same as the material used for the cladding.

6. The ultrasonic wave transmitter of claim 5, wherein the cladding material also serves as the binder and the binder has been formed by fusing the cladding of a first ultrasonic waveguide to the cladding of a second ultrasonic waveguide.

7. The ultrasonic wave transmitter of claim 1, wherein the binder has been potted to interstices between the ultrasonic waveguides.

8. The ultrasonic wave transmitter of claim 1, wherein the core is polymethylmethacrylate.

9. The ultrasonic wave transmitter of claim 1, wherein the core is polyethylene.

10. The ultrasonic wave transmitter of claim 1, wherein the core is a polymer and the core has an internal preload so as to be compressively contained within the cladding.

11. A method of making an ultrasonic acoustic wave transmitter, comprising:
    providing a plurality of ultrasonic waveguides each having a core and cladding that are in intimate contact with each other at their interfacial surfaces, wherein, (a) the core has (i) a first end surface, (ii) a second end surface, and (iii) a longitudinal surface extending between the first and second end surfaces, the core having a first shear-wave propagation velocity ("SWPV"); (b) the cladding substantially surrounds the core to form a cladded core, the cladding comprising polymethylmethacrylate and having a second SWPV,
    wherein the second SWPV is greater than the first SWPV;
    binding the ultrasonic waveguides so as to substantially fix each ultrasonic waveguide relative to the other ultrasonic waveguides.

12. The method of claim 11, wherein the ultrasonic waveguides that are provided are made substantially the same length by cutting the ultrasonic waveguides to a desired length.

13. The method of claim 11, wherein binding is carried out by heating the ultrasonic waveguides to fuse the cladding of at least one ultrasonic waveguide to the cladding of another ultrasonic waveguide.

14. The method of claim 11, wherein binding is carried out by placing a potting material between the ultrasonic waveguides.

15. The method of claim 11, wherein binding is carried out by placing a band around the plurality of ultrasonic waveguides.

16. The method of claim 11, further comprising cutting the bound ultrasonic waveguides so that the first end surfaces of the ultrasonic waveguides lie substantially in a plane.

17. The method of claim 16, further comprising cutting the bound ultrasonic waveguides so that the second end surfaces of the ultrasonic waveguides lie substantially in a plane.

18. The method of claim 11, wherein the core is polymethylmethacrylate.

19. The method of claim 11, wherein the core is polyethylene.

20. The method of claim 11, wherein the core is a polymer, and the core has an internal preload so as to be compressively contained within the cladding.

21. The ultrasonic wave transmitter of claim 1 wherein the plurality of ultrasonic waveguides are adapted to reduce scattering in an ultrasonic energy pulse.

22. The ultrasonic wave transmitter of claim 1 wherein each ultrasonic waveguide is adapted to cause an ultrasonic wave traveling therethrough to be substantially contained in the waveguide due to total internal reflection at the interface of the core and cladding.

23. The ultrasonic wave transmitter of claim 1, wherein the core is polystyrene.

24. The method of claim 11, wherein the core is polystyrene and the cladding is polymethylmethacrylate.

* * * * *